(12) United States Patent
Abbasi et al.

(10) Patent No.: US 11,090,091 B1
(45) Date of Patent: Aug. 17, 2021

(54) CANNULATED ENDPLATE PLUNGER ASSEMBLY

(71) Applicant: Advance Research System, LLC, Edina, MN (US)

(72) Inventors: Hamid R. Abbasi, Edina, MN (US); Kenneth R. Barra, Dallas, GA (US); Stuart J. Olstad, Plymouth, MN (US)

(73) Assignee: Advance Research System, LLC, Edina, MN (US)

( * ) Notice: Subject to any disclaimer, the term of this patent is extended or adjusted under 35 U.S.C. 154(b) by 230 days.

(21) Appl. No.: 16/239,035

(22) Filed: Jan. 3, 2019

Related U.S. Application Data

(60) Provisional application No. 62/613,091, filed on Jan. 3, 2018.

(51) Int. Cl.
*A61B 17/70* (2006.01)
*A61B 17/56* (2006.01)

(52) U.S. Cl.
CPC ...... *A61B 17/7083* (2013.01); *A61B 17/7022* (2013.01); *A61B 17/7076* (2013.01); *A61B 2017/564* (2013.01)

(58) Field of Classification Search
CPC ............ A61B 17/7083; A61B 17/7076; A61B 17/0469; A61B 2017/0409
See application file for complete search history.

(56) References Cited

U.S. PATENT DOCUMENTS

| | | | |
|---|---|---|---|
| 3,875,595 A | 4/1975 | Froning | |
| 4,741,330 A | 5/1988 | Hayhurst | |
| 4,898,156 A | 2/1990 | Gatturna et al. | |
| 5,037,422 A | 8/1991 | Hayhurst et al. | |
| 5,207,679 A | 5/1993 | Li | |
| 5,224,946 A | 7/1993 | Hayhurst et al. | |
| 5,522,845 A | 6/1996 | Wenstrom, Jr. | |
| 5,540,704 A * | 7/1996 | Gordon | A61B 17/0469 112/169 |
| 6,110,210 A | 8/2000 | Norton et al. | |
| 6,113,640 A | 9/2000 | Törmälä et al. | |
| 6,350,284 B1 | 2/2002 | Törmälä | |
| 7,223,289 B2 | 5/2007 | Trieu et al. | |
| 7,491,212 B2 | 2/2009 | Sikora et al. | |
| 7,597,694 B2 * | 10/2009 | Lim | A61B 17/7005 606/86 A |

(Continued)

FOREIGN PATENT DOCUMENTS

WO WO2017/068074 4/2017

*Primary Examiner* — Kevin T Truong
*Assistant Examiner* — Tracy L Kamikawa
(74) *Attorney, Agent, or Firm* — Christensen, Fonder, Dardi & Herbert PLLC

(57) ABSTRACT

A cannulated plunger assembly for setting a tether with anchors on both ends to extend between adjacent vertebrae. The cannulated form enables minimally invasive access to an evacuated space between the vertebral endplates. Each of the anchors are coupled to a respective one of a pair of plunger arms, the plunger arms being configured to deploy the anchors beyond an outer radius of a tubular housing. In some embodiments, in a retracted configuration, the pair of plunger arms are surrounded by the housing, and in a deployed configuration, the pair of plunger arms extend through an open distal end of and beyond an outer radius of the housing to drive the anchors into the vertebral end plates.

14 Claims, 10 Drawing Sheets

(56) References Cited

U.S. PATENT DOCUMENTS

| | | |
|---|---|---|
| 7,655,015 B2 | 2/2010 | Goldfarb et al. |
| 8,460,309 B2 | 6/2013 | Howe |
| 8,864,773 B2 | 10/2014 | Paul et al. |
| 8,864,828 B2 * | 10/2014 | Altarac .............. A61B 17/7065 623/17.11 |
| 2003/0097150 A1 | 5/2003 | Fallin et al. |
| 2004/0087975 A1 | 5/2004 | Lucatero et al. |
| 2005/0203529 A1 | 9/2005 | Boehm, Jr. et al. |
| 2010/0094425 A1 | 4/2010 | Bentley et al. |
| 2012/0253392 A1 | 10/2012 | Bentley et al. |
| 2013/0023911 A1 | 1/2013 | Esanu |
| 2015/0127021 A1 | 5/2015 | Harris et al. |

* cited by examiner

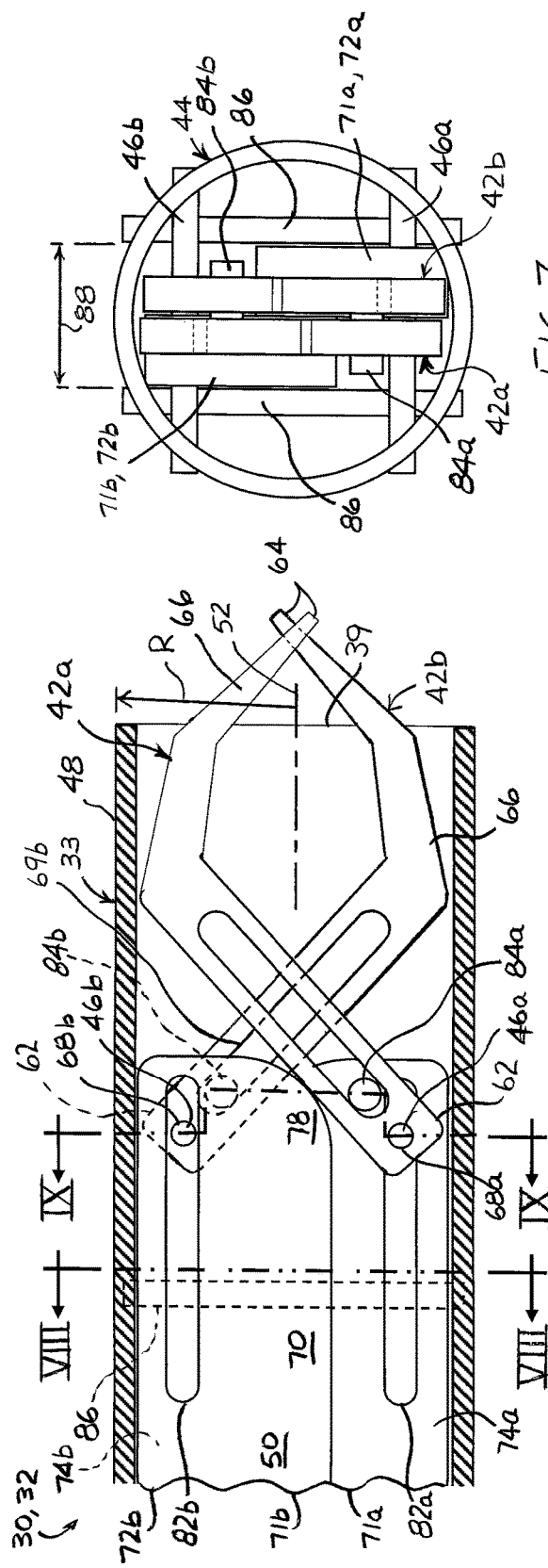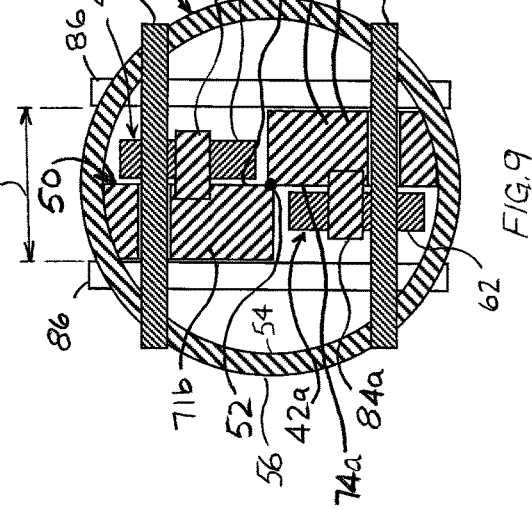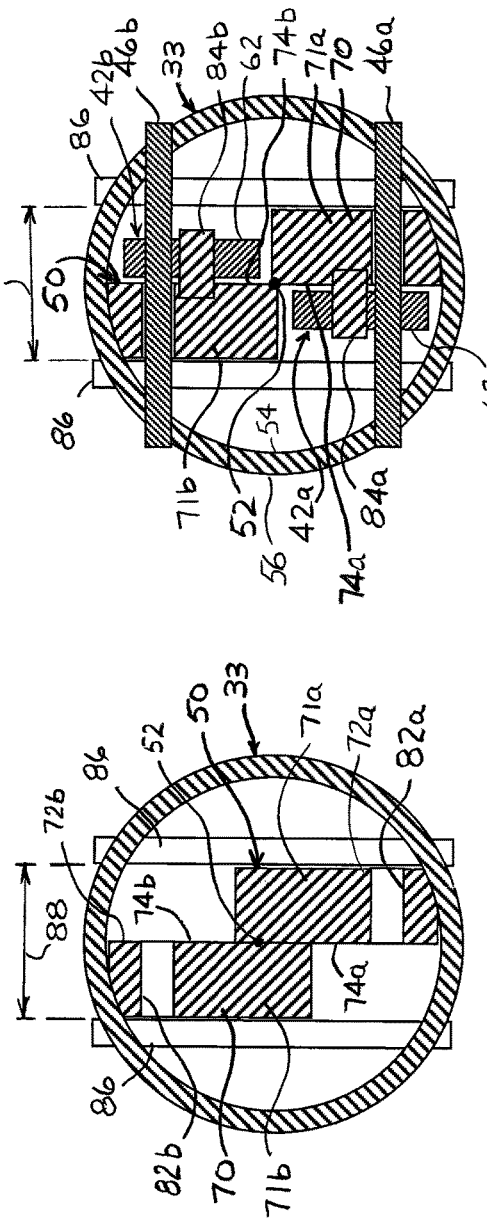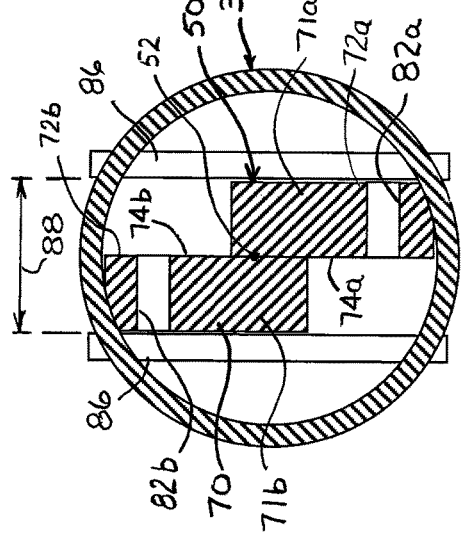

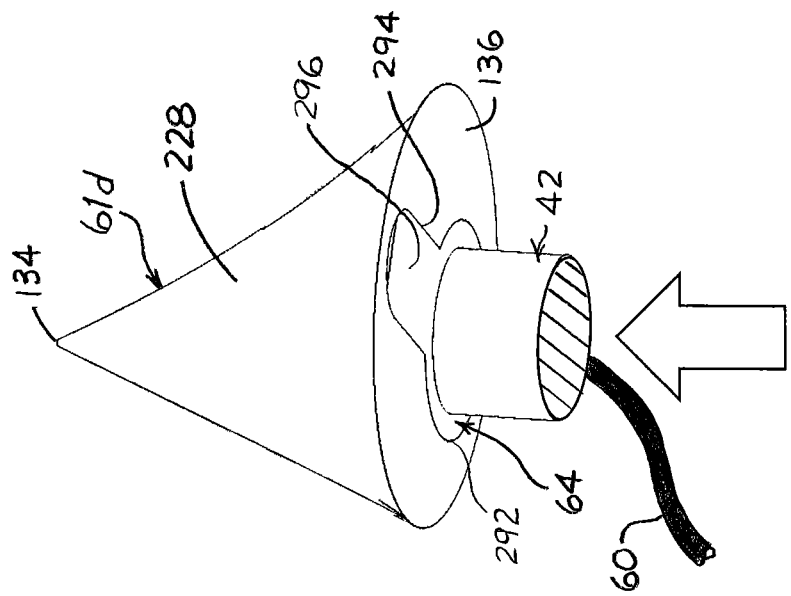
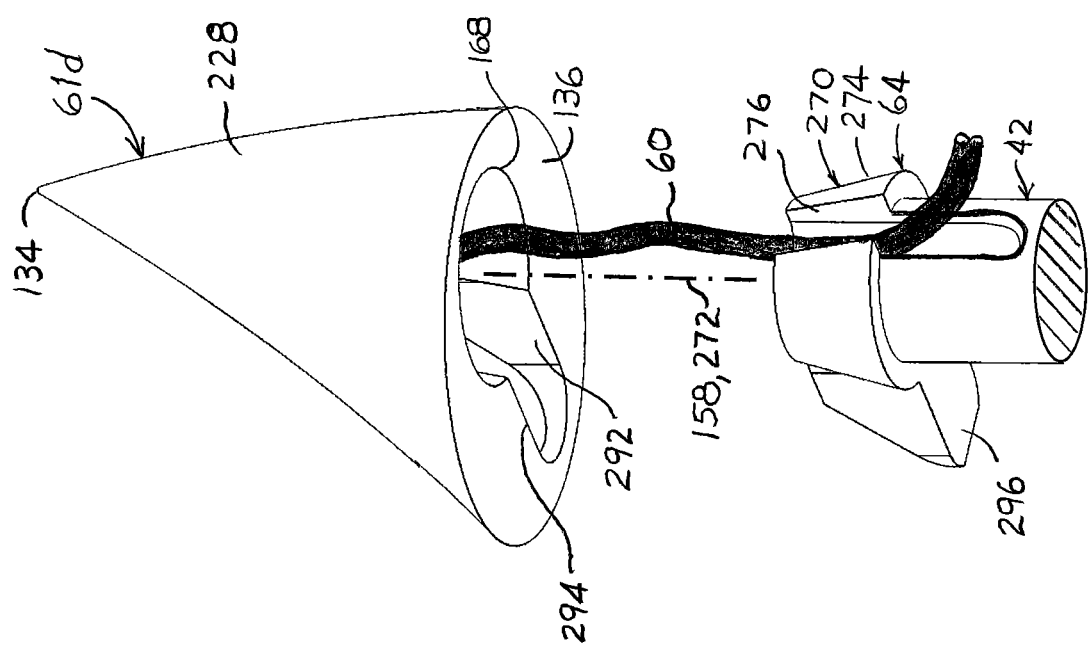

CANNULATED ENDPLATE PLUNGER ASSEMBLY

RELATED APPLICATION

This application claims the benefit of U.S. Provisional Patent Application No. 62/613,091, filed Jan. 3, 2018, the disclosure of which is hereby incorporated by reference herein in its entirety.

FIELD OF THE DISCLOSURE

The disclosure is directed to methods and tools for spinal fusion therapy, and more specifically to methods and tools for implanting tissue growth-promoting devices between adjacent vertebrae.

SUMMARY OF THE DISCLOSURE

In various embodiments, an anchored tether is disclosed including a tether with anchors affixed thereto. The tether is anchored to and extended between adjacent vertebral endplates to guide and promote tissue growth between the endplates after evacuation of the nucleus in a spinal fusion surgical process.

In various embodiments, deployment of the tether with anchors is performed with a cannulated plunger assembly. The cannulated form enables minimally invasive access to the evacuated space between the vertebral endplates. Each of the anchors are coupled to a respective one of a pair of plunger arms, the plunger arms being disposed at the distal end of a tubular housing and configured to deploy the anchors beyond an outer radius of the housing and, in some embodiments, beyond an outer radius of the cannula. An open end of the cannulated plunger assembly is positioned between the vertebral endplates. Upon deployment, one of the plunger arms extends in the superior direction and the other in an inferior direction to drive the anchors of the tether into the respective superior and inferior end plates. The plunger arms are then retracted back at least partially within the housing so that the plunger arms are within the inner radius of the cannula for minimally invasive withdrawal of the cannulated plunger assembly.

The plunger arms and anchors are configured to be self-releasing, so that once the anchors are mounted into the vertebral end plates, the plunger arms are released by mere retraction of the plunger arms. The anchors also include features that enable securing of the tether thereto.

Structurally, in various embodiments of the disclosure, a plunger assembly is disclosed for setting tether with anchors affixed thereto for extending between adjacent vertebrae, comprising a tubular housing defining a central axis and having an open distal end, a pair of plunger arms disposed at least partially within the tubular housing, each of the plunger arms being mounted to a respective pivot pin, the pivot pin being mounted to and extending laterally through the housing, and a drive assembly disposed in the tubular housing, the drive assembly configured to translate parallel to the central axis and toward the open distal end to rotate the pair of plunger arms from a retracted configuration to a deployed configuration, the drive assembly configured to translate parallel to the central axis and toward the open distal end to rotate the pair of plunger arms from the retracted configuration to the deployed configuration. The plunger assembly may include an actuation handle affixed to a proximal end of the tubular housing, the actuation handle being coupled to the drive assembly for translation of the drive assembly along the central axis. In some embodiments, the actuation handle is a KERRISON handle.

In some embodiments, in the retracted configuration, the pair of plunger arms are surrounded by the tubular housing, and in the deployed configuration, the pair of plunger arms extend through the open distal end and beyond an outer radius of the housing. In some embodiments, the drive mechanism is coupled to the pair of plunger arms in a camming arrangement. In some embodiments, the camming arrangement includes a pair of cam slots, each defined by a corresponding one of the pair of arms, and a pair of cam pins, each extending from the drive assembly and being disposed in a corresponding one of the pair of cam slots. In some embodiments, the camming arrangement includes a pair of arcuate reliefs formed at a distal end of the drive assembly, each contacting a corresponding one of the pair of plunger arms to drive the plunger arms from the retracted configuration into the deployed configuration.

Each of the pair of plunger arms may include a distal end portion configured to accept a respective anchor. In some embodiments, the distal end portion is configured to cant the respective anchor with respect to the plunger arm to generally align the anchor with an arc through which the anchor travels during deployment. The distal end portion may include a tapered surface for release of the anchor. In some embodiments, the distal end portion is shaped as a frustum. The frustum may define an open slot that is recessed from the tapered surface to allow passage of the tether from the anchor.

In various embodiments of the disclosure, a tether with anchors to extend between adjacent vertebrae is disclosed, comprising a tether having opposed ends and a pair of anchors, one each attached to a respective one the opposed ends of the tether. Each anchor may include a body including an outer surface that extends from a distal extremity to a proximal base surface, the body defining a mounting recess that extends along a mounting axis, the mounting recess defining an opening on the base surface and defining a tapered surface that extends from the base surface into the mounting recess, the tapered surface sloping away from the mounting axis at the opening in a proximal direction. In some embodiments, the anchor includes a tether receptacle that defines an open slot and an external socket coincident with the open slot, the open slot and the external socket being accessible from the outer surface, the open slot being accessible from the base surface, the tether being coupled to tether receptacle. A knot may be formed at a respective end of the tether, the knot being disposed in the external socket, the tether extending through the open slot. In an alternative embodiment, the tether comprises a ferrule having a proximal face and a distal face and an outer surface that extends from the proximal face to the distal face, the ferrule defining a tether socket accessible from the distal face of the ferrule, the ferrule defining an open slot that extends axially through the proximal face and the distal face of the ferrule and radially through the outer surface of the ferrule, the open slot of the ferrule being in fluid communication with the tether socket. A knot may be formed at a respective end of the tether, the knot being disposed in the tether socket, the tether extending through the open slot of the ferrule in a proximal direction. The outer surface of the ferrule may be tapered to define a first angle relative to a central axis of the ferrule, the first angle of outer surface of the ferrule sloping away from the central axis in a proximal direction.

In some embodiments, the anchor defines an internal socket configured to receive the ferrule in an interference fit. The internal socket may be distal to the mounting recess and may be concentric about the mounting axis. An inner surface of the internal socket may include a tapered surface that defines a second angle that slopes away from the mounting axis in the proximal direction, the second angle being greater than the first angle. In some embodiments, the mounting recess defines a first radius relative to the mounting axis, the distal face of the ferrule defines a second radius relative to the central axis, the proximal face of the ferrule defines a third radius relative to the central axis, the second radius is less than the first radius, and the third radius is greater than the first radius.

In some embodiments, the outer surface of the anchor defines a profile that is axisymmetric about a body axis that extends through the distal extremity. The profile may be substantially triangular. The distal extremity may be pointed. The body axis may be concentric with the mounting axis. In some embodiments, the body axis may be linear; in other embodiments, the body axis may be arcuate. In some embodiments, the mounting recess defines a frustoconical void. In some embodiments, the recess and the opening may be asymmetrical about the mounting axis. The recess and the opening may define a keyway. In some embodiments, the body axis is substantially congruent with a radius of an arc through which the anchor travels during deployment.

BRIEF DESCRIPTION OF THE DRAWINGS

FIG. 6 is the partial sectional, side elevational view of a cannulated plunger assembly (including guide pins) in the retracted configuration of FIG. 2, identifying various sectional views thereof according to an embodiment of the disclosure;

FIG. 7 is an end view of the cannulated plunger assembly of FIG. 6, according to an embodiment of the disclosure;

FIG. 8 is a sectional view at line VIII-VIII of FIG. 6, according to an embodiment of the disclosure;

FIG. 9 is a sectional view at line IX-IX of FIG. 6, according to an embodiment of the disclosure;

FIG. 23 is a lower perspective view of a keyed arcuate anchor aligned with a keyed plunger arm distal end portion according to an embodiment of the disclosure; and FIG. 24 is a lower perspective view of the keyed arcuate anchor positioned on the keyed plunger arm distal end portion of FIG. 23 according to an embodiment of the disclosure.

DETAILED DESCRIPTION

Figure 1A:
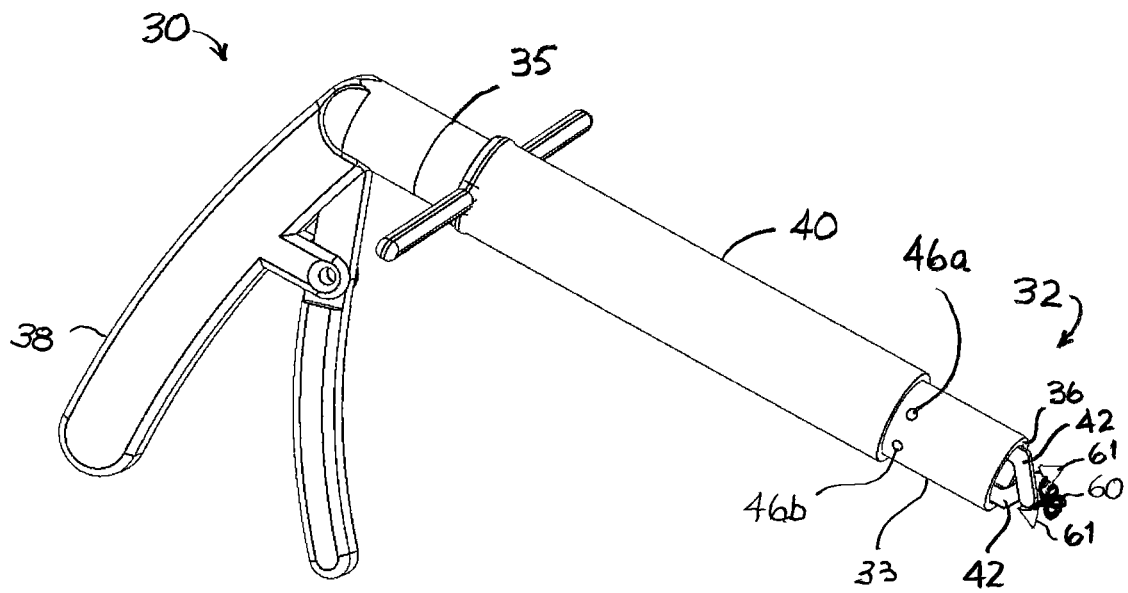
FIG. 1A is a perspective view of a cannulated plunger assembly in a retracted configuration according to an embodiment of the disclosure.
Figure 1B:
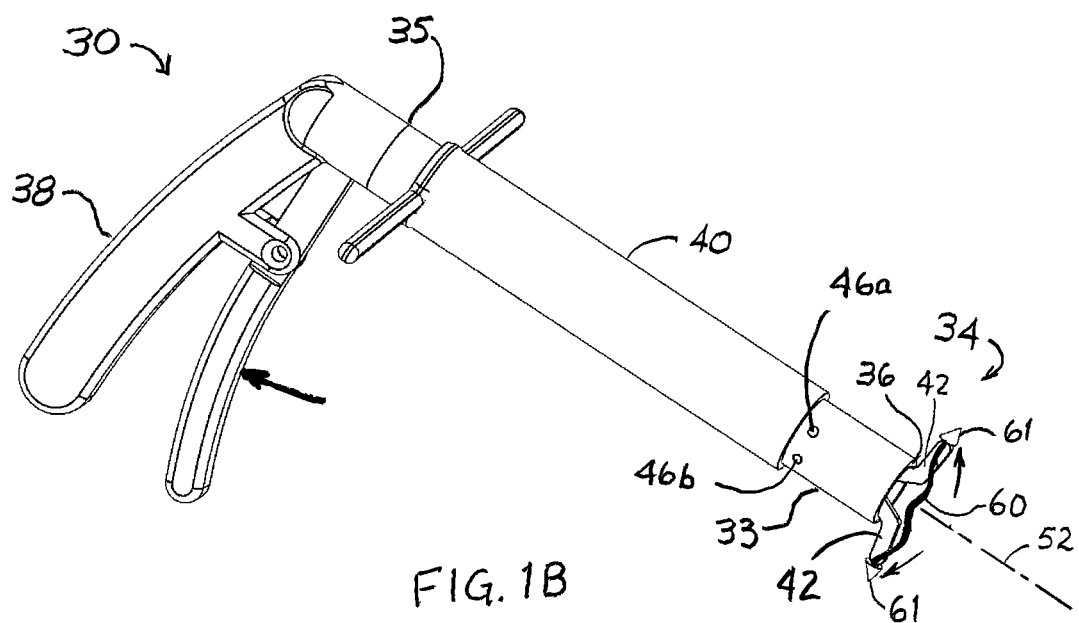
FIG. 1B is a perspective view of a cannulated plunger assembly in a deployed configuration according to an embodiment of the disclosure.
Figure 2:
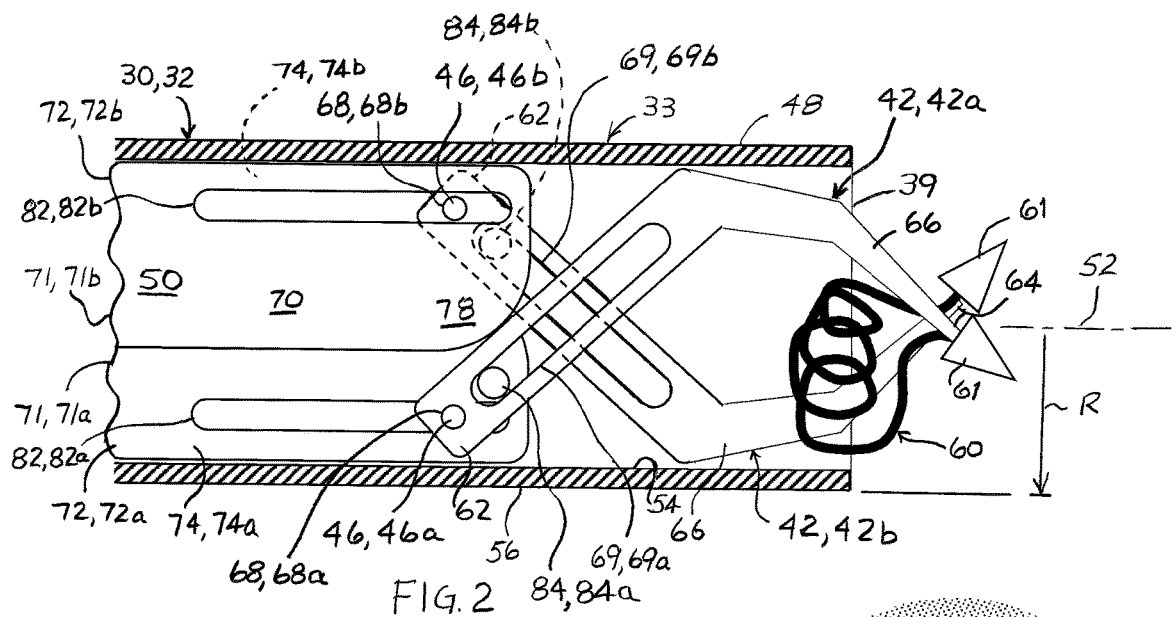
FIG. 2 is a partial sectional, side elevational view of a cannulated plunger assembly with a tether having anchors mounted thereto in a retracted configuration according to an embodiment of the disclosure.

Referring to FIGS. 1A and 1B, a cannulated plunger assembly 30 is depicted in a retracted configuration 32 and a deployed configuration 34, respectively, according to embodiments of the disclosure. The cannulated plunger assembly 30 includes a tubular housing 33 having a proximal end 35 and a distal end 36, with an actuation handle 38 affixed to the proximal end 35. The distal end 36 of the tubular housing 33 defines an open end 39 through which a pair of articulating plunger arms 42 are deployed and retracted. The cannulated plunger assembly 30 can be deployed through a cannula 40.

The actuation handle 38 may be a KERRISON handle (depicted) The KERRISON handle may include a ratcheting mechanism (not depicted) that prevents retraction until a ratchet follower of the ratcheting mechanism is released. In some embodiments, the KERRISON handle advances a ratcheting mechanism (not depicted) akin to a caulk dispenser. Other handles that effect a translating motion when actuated include a threaded, rotating knob (not depicted) that translates a link or plunger when rotated. Impact mechanisms (not depicted) are also contemplated, for example a trigger-actuated mechanism that releases potential (spring) energy to transfer an impact load to a translating mechanism that actuates the plunger arms, or an axial handle with an impact cap that is struck with a mallet to impart the impact load.

Referring to FIGS. 2 through 11, the distal end 36 of the cannulated plunger assembly 30 is depicted in the retracted configuration 32 and the deployed configuration 34, respectively, according to an embodiment of the disclosure. As outlined in the Brief Description of the Figures, FIGS. 2 through 11 depict the components of the cannulated plunger assembly 30 in various states of operation, with some depicting only certain components of the plunger assembly 30 for clarity. The articulating plunger arms 42 are referred to individually as plunger arms 42a and 42b and are mounted within the tubular housing 33 to respective fixed pivot pins 46a and 46b. In some embodiments, the fixed pivot pins 46 are mounted to a wall 48 of the tubular housing 33. A drive assembly 50 is contained within the tubular housing 33 and configured to translate parallel to a central axis 52 of the tubular housing 33. A tether 60 with anchors 61 at both ends may be mounted to the plunger arms 42.

The shaft wall 48 includes an interior surface 54 and an exterior surface 56. In some embodiments, the tubular housing 33 is tubular and cylindrical and the shaft wall 48 continuous about the central axis 52. The shaft wall 48 may define any of a variety of cross-sections, such as circular (depicted), elliptical, oblong, square, rectangular, or polygonal. The tubular housing 33 further defines an outer dimension R, which, for a circular cross-section, is the outer radius.

Each plunger arm 42 includes a proximal end portion 62 and a distal end portion 64, with a generally arcuate portion 66 at the distal end portion 64. Plunger arms 42a and 42b each define a respective mounting aperture 68a and 68b at the proximal end portion 62 through which the respective fixed pivot pin 46 passes. In some embodiments, the mounting apertures 68 are dimensioned to rotate about the fixed pivot pin 46. Plunger arms 42a and 42b each define a respective cam slot 69a and 69b that extends distal to the mounting aperture 68. In the depicted embodiment, the cam slots 69 are linear; however, arcuate cam slots are also contemplated.

The drive assembly 50 includes a drive shaft 70. The drive shaft may include two flat bar portions 71a and 71b that overlap each other along the central axis 52 to define two flange portions 72a and 72b (see, e.g., FIG. 8) that are offset from the central axis 52, with an inner face 74a and 74b of each flange portion 72a and 72b extending coplanar from the central axis 52. In the depicted embodiment, the drive shaft 70 includes a distal end portion 78 wherein each flat bar portion 71a and 71b defines an arcuate relief 76a and 76b, respectively, each extending laterally from adjacent the inner face 74b and 74a of the other of the flange portions 72b and 72a. The flat bar portions 71 may be joined together by welding, riveting, with fasteners, or by any other techniques available to the artisan. Alternatively, instead of two flat bar portions, the drive shaft 70 may be formed to include the disclosed shapes and features by techniques available to the artisan, including machined from a forged bar or casting, molded, stamped, and printed with a three-dimensional printer.

Each of the flanged portions 72 of the drive assembly 50 defines elongate slots 82a and 82b, through which the respective fixed pivot pins 46a and 46b pass. The drive assembly 50 further includes cam pins 84a and 84b which extend laterally from and normal to the inner faces 74a and 74b, respectively, of the drive shaft 70 and into the cam slots 69a and 69b, respectively. In some embodiments, the drive assembly 50 is centered within the tubular housing 33 with guide pins 86, as depicted in FIGS. 6 through 11. In the depicted embodiment, the guide pins 86 extend substantially parallel to the inner faces 74, and are laterally separated by a dimension 88 that allows the drive shaft 70 to pass between the guide pins 86.

Herein, the plunger arms 42a and 42b, the fixed pivot pins 46a and 46b, the mounting apertures 68a and 68b, the cam slots 69a and 69b, the flat bar portions 71a and 71b, the flange portions 72a and 72b, the arcuate reliefs 76a and 76b, the elongate slots 82a and 82b, and the cam pins 84a and 84b are referred to collectively and generically as plunger arm(s) 42, fixed pivot pin(s) 46, mounting aperture(s) 68, cam slot(s) 69, flat bar portion(s) 71, flange portion(s) 72, arcuate relief(s) 76, elongate slot(s) 82, and cam pin(s) 84, respectively.

Figure 3:
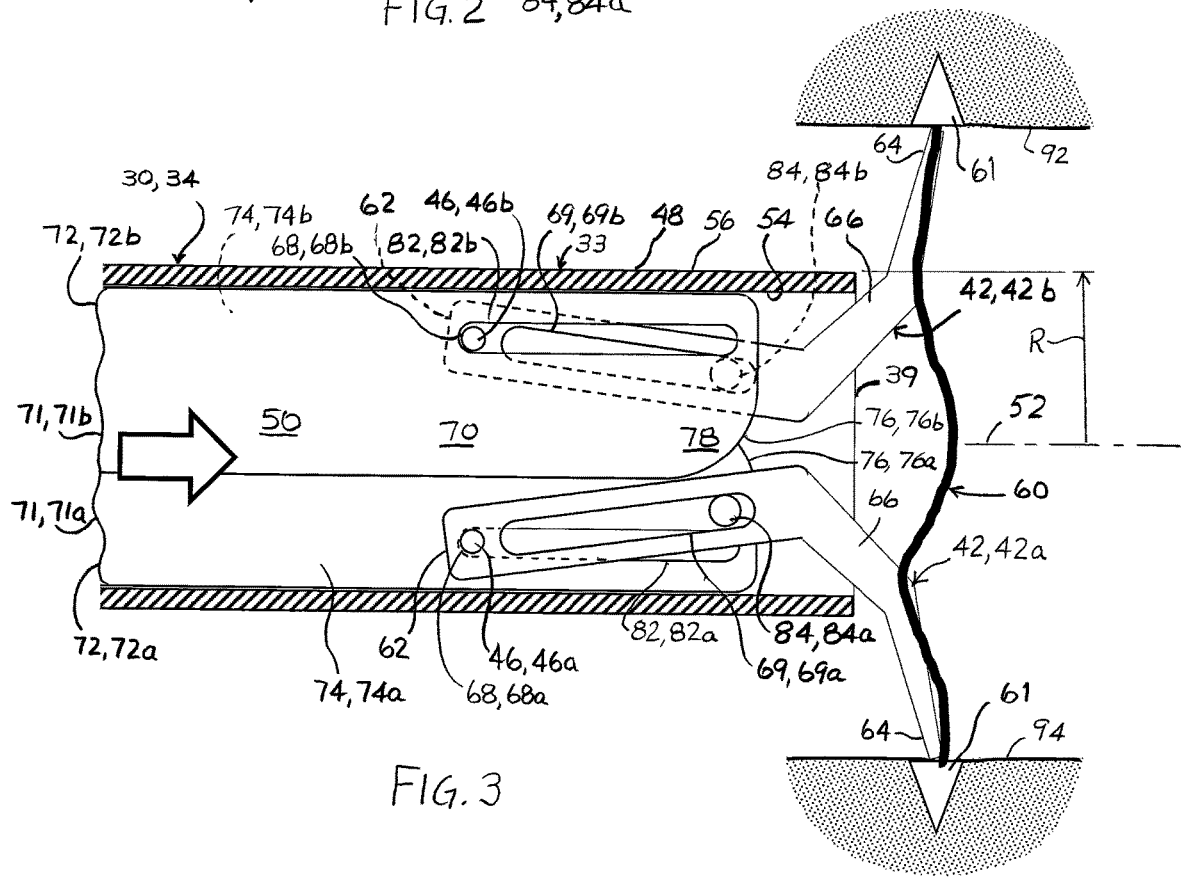
FIG. 3 is a partial sectional, side elevational view of the cannulated plunger assembly and tether with anchors of FIG. 1 in a deployed configuration with the anchors of the anchored tether affixed to adjacent vertebral endplates according to an embodiment of the disclosure.
Figure 4:
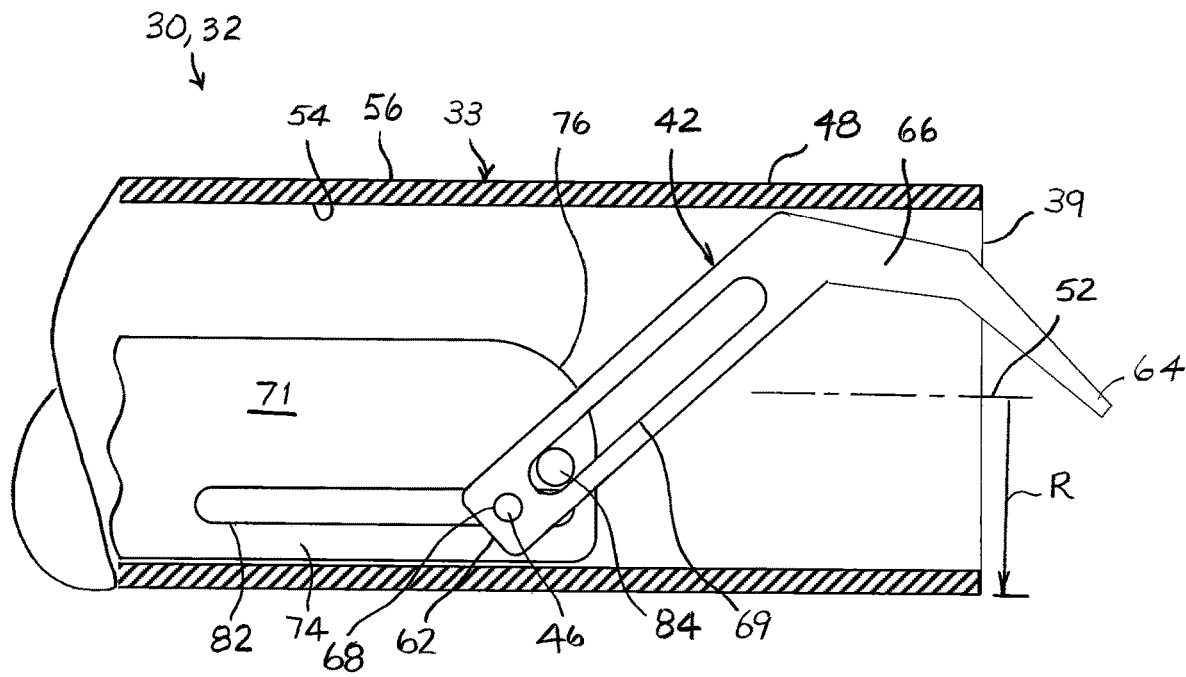
FIG. 4 depicts a single plunger arm and a portion of the drive assembly that drives the plunger arm of the cannulated plunger assembly in the retracted configuration of FIG. 2, with extraneous components removed for clarity.
Figure 5:
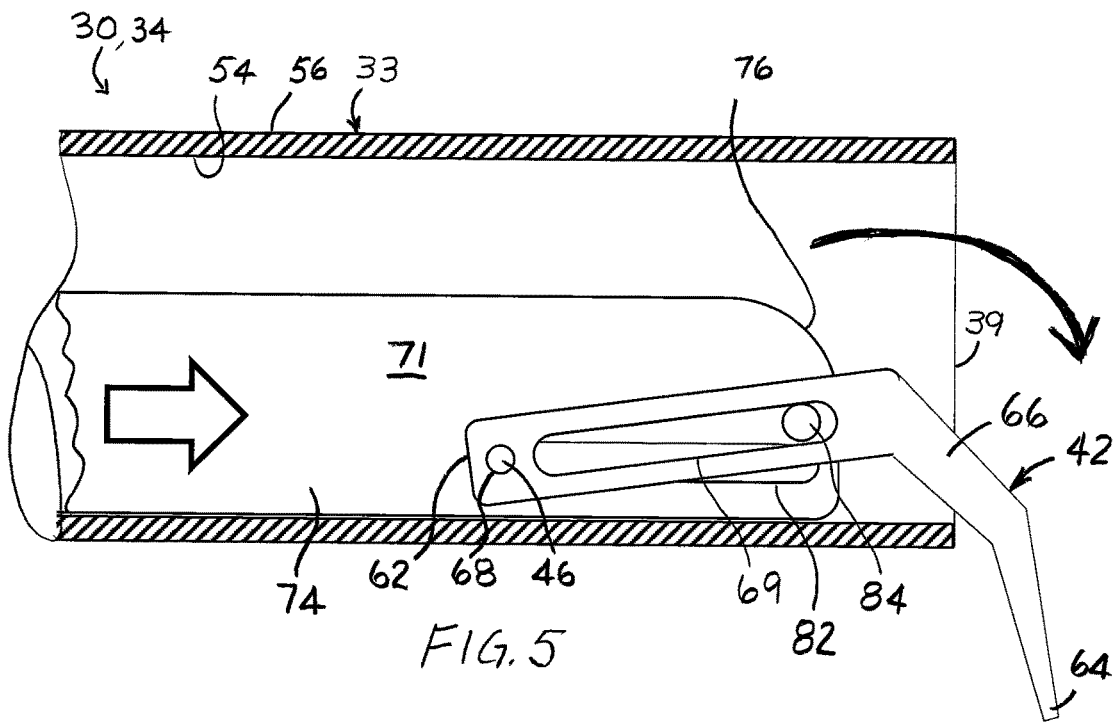
FIG. 5 depicts the single plunger arm and portion of the drive assembly that drives the plunger arm of the cannulated plunger assembly in the deployed configuration of FIG. 3, with extraneous components removed for clarity.
Figure 11:
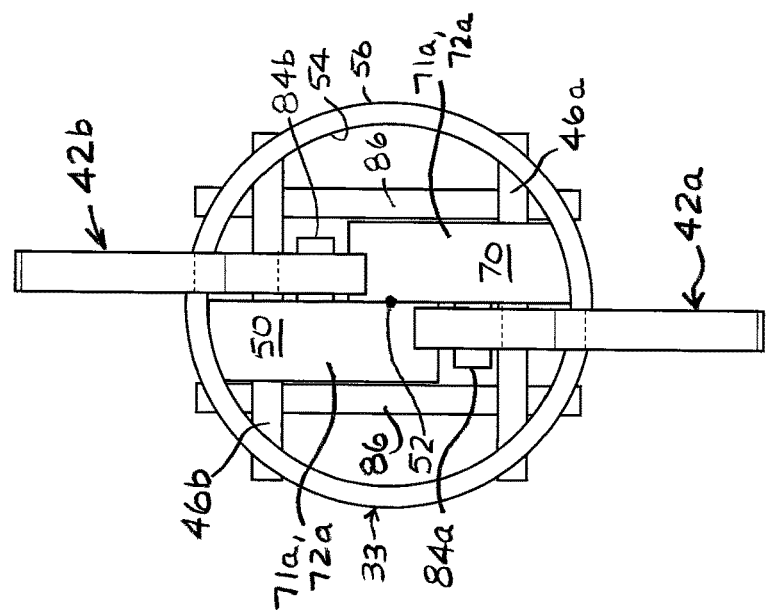
FIG. 11 is an end view of the cannulated plunger assembly of FIG. 10, according to an embodiment of the disclosure.
Figure 10:
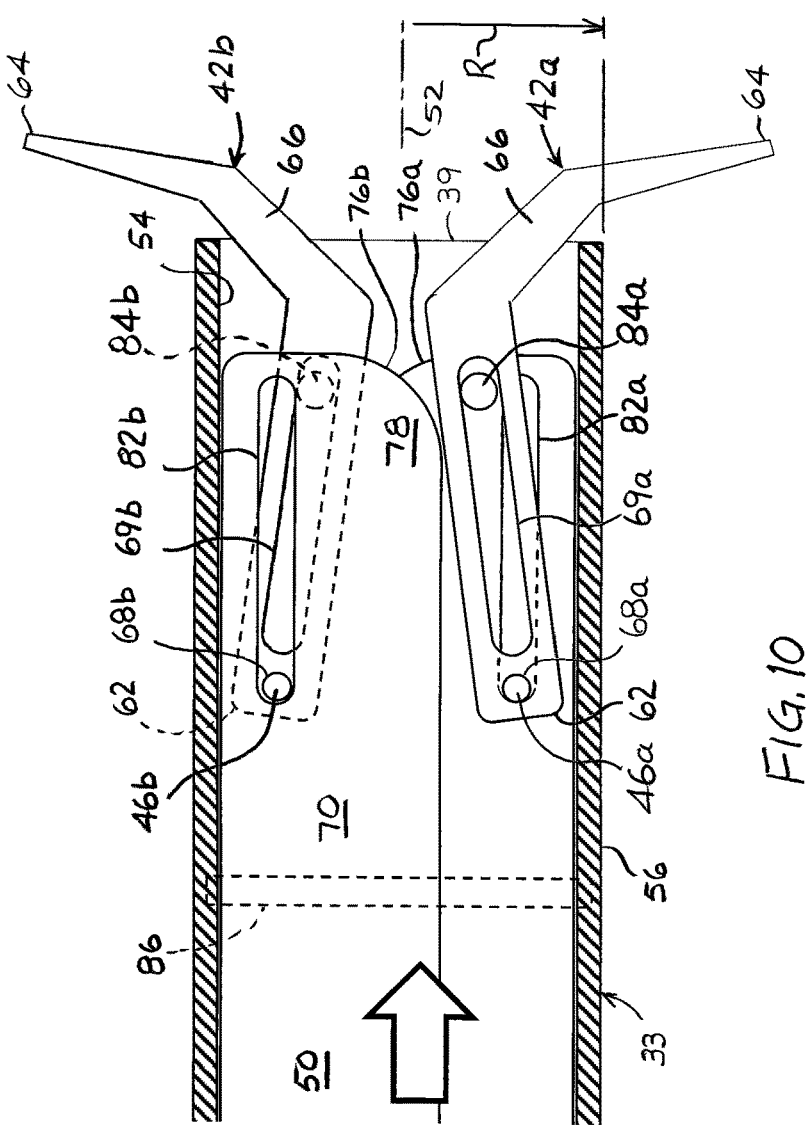
FIG. 10 is the partial sectional, side elevational view of a cannulated plunger assembly (including guide pins) in the deployed configuration of FIG. 3, according to an embodiment of the disclosure.
Figure 14:
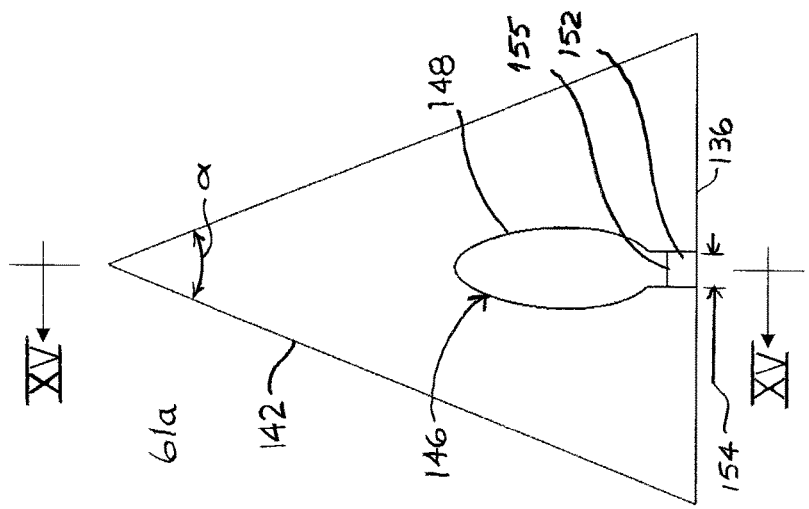
FIG. 14 is an elevational view of the conical anchor of FIG. 12 according to an embodiment of the disclosure.
Figure 15:
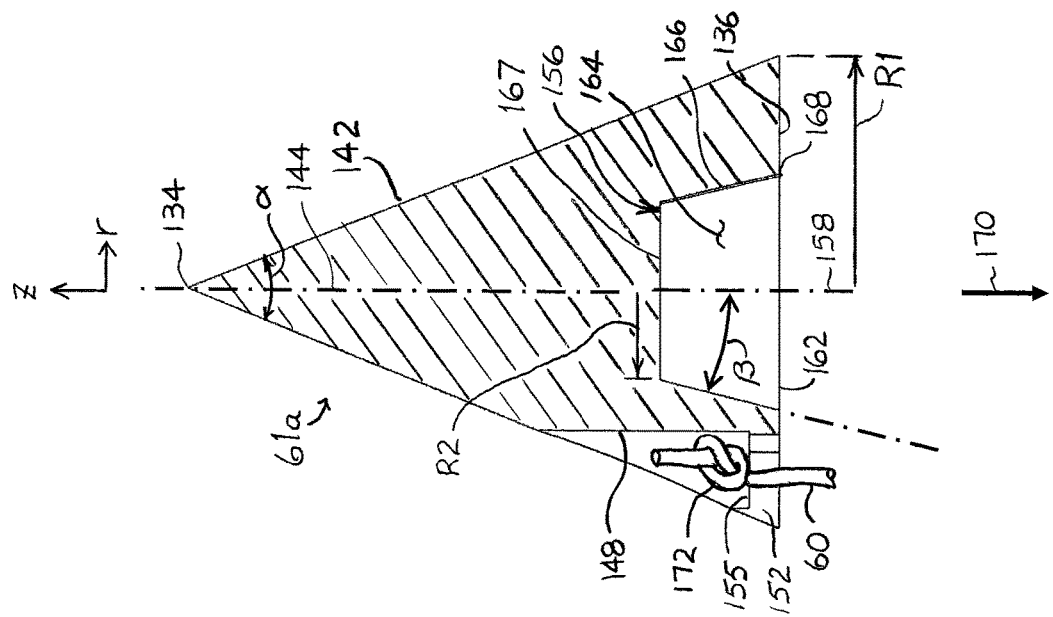
FIG. 15 is a sectional view of the conical anchor at plane XV-XV of FIG. 14 according to an embodiment of the disclosure.
Figure 12:
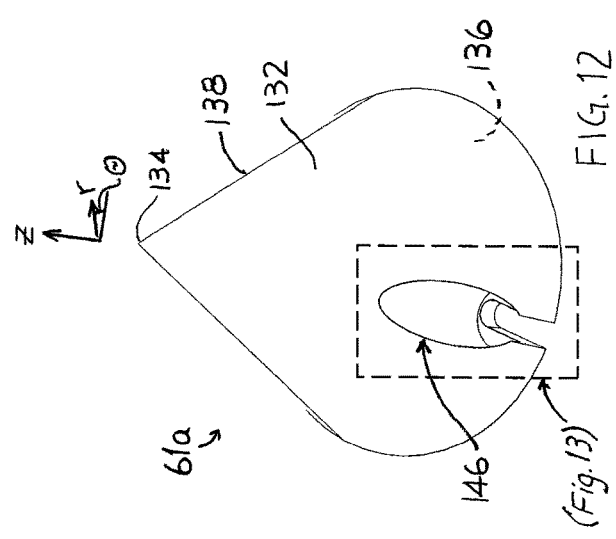
FIG. 12 is an upper perspective view of a conical anchor according to an embodiment of the disclosure.
Figure 13:
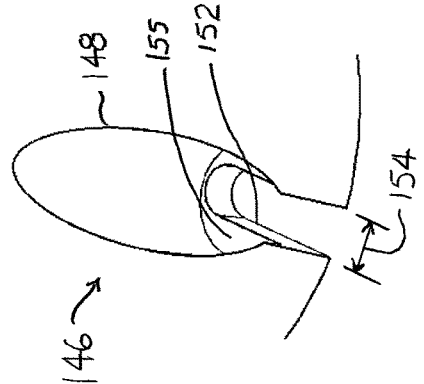
FIG. 13 is an enlarged, partial view of the conical anchor of FIG. 12 according to an embodiment of the disclosure.
Figure 17:
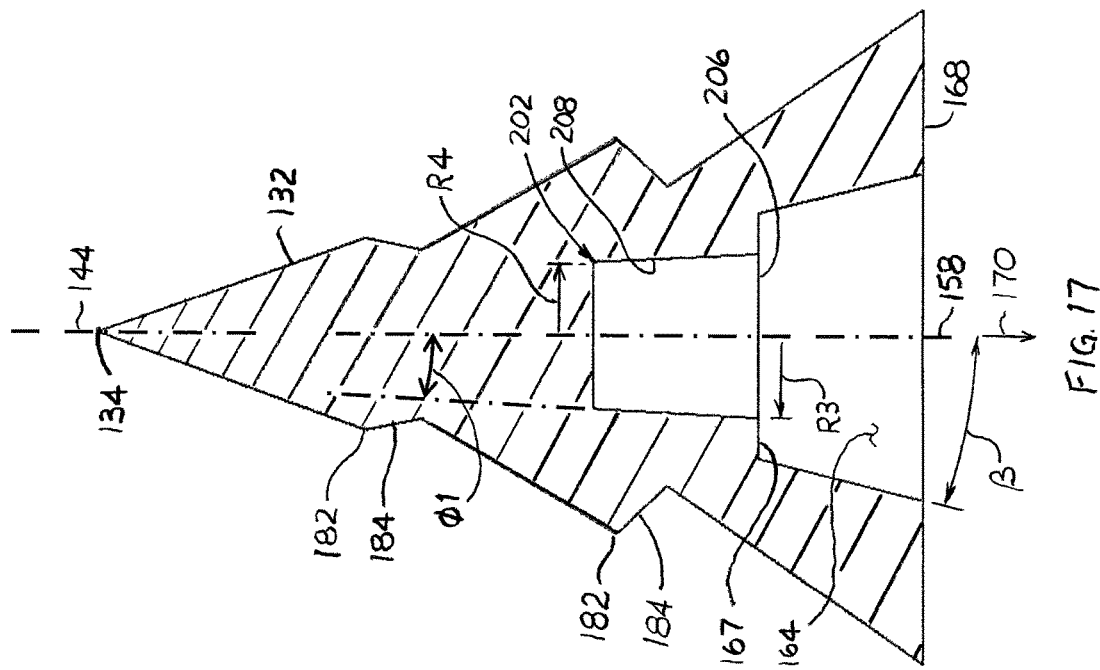
FIG. 17 is an elevational sectional view of the barbed anchor of FIG. 16 according to an embodiment of the disclosure.
Figure 16:
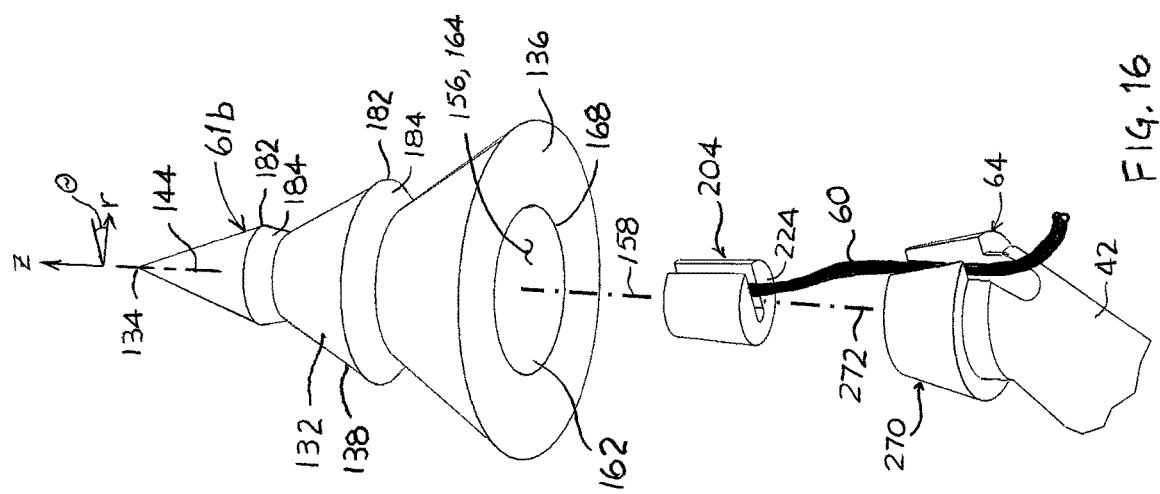
FIG. 16 is a lower perspective view of a barbed anchor, ferrule, and plunger arm distal end portion according to an embodiment of the disclosure.
Figure 18:
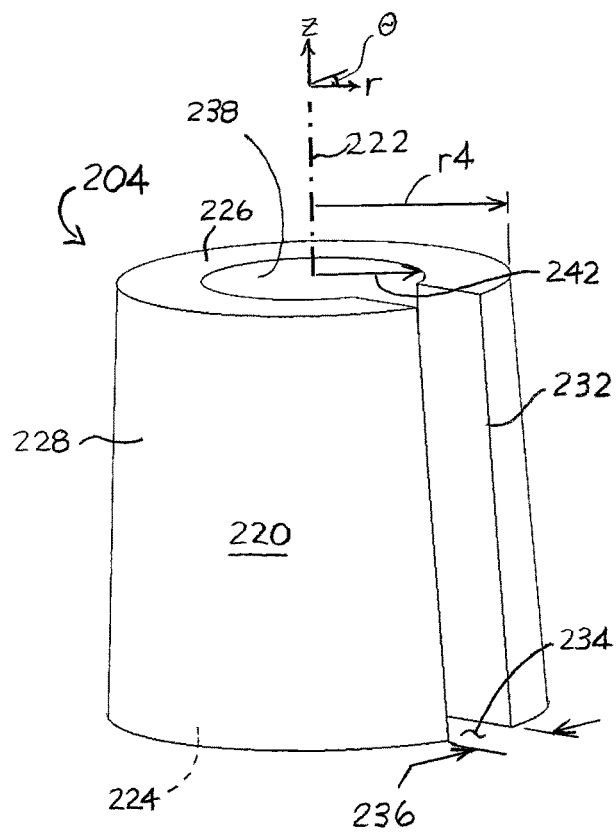
FIG. 18 is an upper perspective view of the ferrule of FIG. 16 according to an embodiment of the disclosure.
Figure 19:
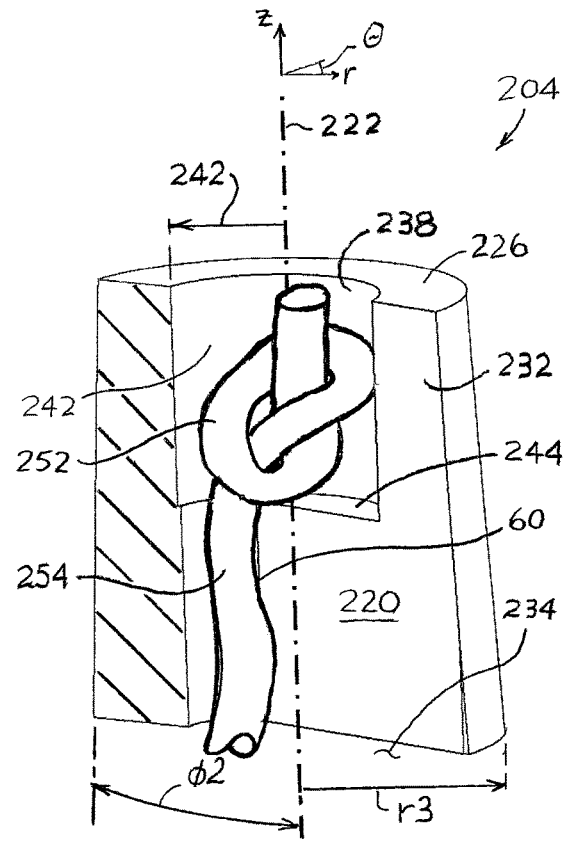
FIG. 19 is a sectional view of the ferrule of FIG. 18 with a tether mounted therein according to an embodiment of the disclosure.
Figure 20:
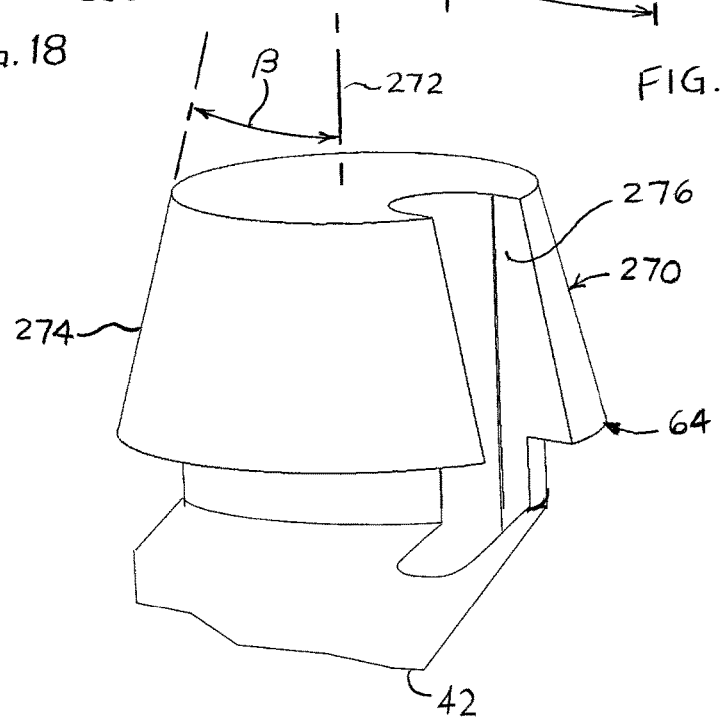
FIG. 20 is an enlarged, upper perspective view of the plunger arm distal end of FIG. 16 according to an embodiment of the disclosure.

In operation, the distal open end 39 is inserted into an open space between two vertebral endplates 92 and 94, which may be accessed via cannula 40. To deploy the plunger arms 42 of the cannulated plunger assembly 30, the drive assembly 50 is translated toward the distal open end 39 of the tubular housing 33 (FIG. 3). The forward translation causes the cam pins 84 to slidingly engage the cam slots 69, thereby causing the plunger arms 42 to rotate away from the interior surface 54 of the shaft wall 48 and through the open end 39. The rotation away from the interior surface 54 of the shaft wall 48 causes the distal end portions 64 of the plunger arms 42 to move radially outward, beyond the outer dimension R of the exterior surface 56 of the shaft wall 48. This action drives the anchors 61 into the respective endplates 92 and 94. In some embodiments, the radially outward rotation also causes the distal end portions 64 to move beyond an outer surface of the cannula 40.

Functionally, having the plunger arms 42 pivotally mounted to the fixed pivot pins 46 causes the plunger arms 42 to produce the same, repeatable motion with respect to the open end 39 of the tubular housing 33. In this way, by knowing the location of the open end 39 of the tubular housing 33 (for example by fluoroscopic or other imaging techniques) the surgeon can predict with reasonable certainty where the anchors 61 will be seated within the endplates 92, 94. By having the plunger arms 42 driven by the pin-and-slot arrangement of the cam pins 84 within the cam slots 69, both the deployment and retraction of the are positively driven, instead of relying on some passive mechanism, such as spring biasing, to effect either deployment or retraction. The elongate slots 82 enable the drive assembly 50 slide over the fixed pivot pins 46 during translation within the tubular housing 33. The pin-and-slot arrangement of the pivot pins 46 and the elongate slots 82 further facilitate a stop mechanism for the drive assembly 50 as the pivot pins 46 engage the ends of the elongate slots 82 to define the extremities of the deployed and retracted configurations 32 and 34. The guide pins 86 keep the drive assembly 50 centered within the tubular housing 33 and within a zone where the drive shaft 70 does not generate unwanted resistance to sliding against the interior surface 54 of the shaft wall 48, thereby preventing the drive mechanism 50 from jamming during deployment and retraction.

The arcuate reliefs 76 enable the plunger arms 42 to rotate during deployment and retraction without interference from the distal end portion 78 of the drive shaft 70. It is also contemplated that the arcuate reliefs 76a and 76b be arranged and configured to engage the other of the plunger arms 42b and 42a, respectively, so that the arcuate reliefs 76 contact the plunger arms 42b and 42a to act as cam surfaces that additionally drive the plunger arms 42 to assist in deployment, while not interfering with the plunger arms 42 during retraction. In this way, during deployment, the plunger arms 42 can be driven by both the cam pins 84 and the arcuate reliefs 76 during the higher stress operation of implanting the anchors 61 into the vertebral endplates 92 and 94.

Referring to FIGS. 12 through 24, various anchors 61 are depicted according to embodiments of the disclosure. The anchors 61 are referred to generically and collectively by reference character 61, with specific embodiments being referenced by reference character 61 followed by a letter suffix (e.g., "conical anchor 61a"). The anchors 61 and certain components may be described in terms of respective local r-θ-z coordinate systems of arbitrary origin along a central axis (e.g., along the body axis 144 of the anchor 61 or along the central axis 222 of the ferrule 204). A direction congruent with the r coordinate is herein referred to as "radial", a direction congruent with the θ coordinate is herein referred to as "tangential", and a direction congruent with the z coordinate is herein referred to as "axial". It is understood that combination of specific aspects of various embodiments of the anchors 61, even though not depicted herein, are within the grasp of a person of ordinary skill in the art in view of the content of this disclosure, and therefore considered to be within the scope of any claimed invention herein.

In FIGS. 12 through 15, a conical anchor 61a is depicted according to an embodiment of the disclosure. The conical anchor 61a includes a body 132 having a pointed distal extremity 134 and a proximal base surface 136, with an outer surface 138 extending from the pointed distal extremity 134 to the proximal base surface 136. The outer surface 138 may be conical, outlining a triangular profile 142 that defines an apex angle α at the pointed distal extremity 134, the angle α being coplanar with a body axis 144 that passes through the pointed distal extremity 134. In some embodiments, the conical body 132 defines a tether receptacle 146 that extends through the outer surface 138 and the proximal base surface 136. The tether receptacle 146 may define an external socket 148 and an open slot 152, the open slot 152 defining a gap 154 that is smaller in the tangential dimension θ of the r-θ-z coordinate system than the external socket 148. A shoulder 155 is defined at a transition between the external socket 148 and the open slot 152. The external socket 148 is so-named because it extends from and is accessible from the outer surface 138 of the anchor 61a.

The proximal base surface 136 defines a mounting recess 156 that extends along a mounting axis 158, the mounting recess 156 defining an opening 162 on the proximal base surface 136 having a radius R1. In some embodiments, the mounting recess 156 defines a frustoconical void 164 bounded radially by a tapered surface 166 and axially by a distal surface 167, a maximum radius R2 being defined at a distal end of the tapered surface 166. The tapered surface 166 defines an angle β relative to the mounting axis 144 at a perimeter 168 of the opening 162, such that the tapered surface 166 slopes away from the mounting axis 158 at the perimeter 168 of the opening 162 in a proximal direction 170.

In assembly, a knot 172 is formed proximate an end of the tether 60 and disposed in the external socket 148, the knot 172 being of greater radial dimension than the tangential dimension of the open slot 152. The tether 60 is slipped into the open slot 152 so that the knot 172 rests on the shoulder 155 of the external socket 148 and the tether 60 extends proximally from the conical anchor 61a.

Functionally, the arrangement of the knot 172 within external socket 148 enables the tether 60 to be coupled to the conical anchor 61a. Because the knot 172 is of greater radial dimension than the gap 154 of the open slot 152, the knot 172 is obstructed by the shoulder 155 of the external socket 148 and will not pass through the gap 154 of the conical anchor 61a. When the conical anchor 61a is set into the vertebral end plate 92, 94, the knot 172 is captured within the external socket 148 between the shoulder 155 and the bone of the vertebral end plate 92, 94.

Optionally, instead of forming a knot at the end of the tether 60, a sleeve (not depicted) may be crimped on to the end of the tether 60, the crimped sleeve having a greater diameter than the gap 154. Optionally, the tether 60 can be affixed to a ferrule and seated in the external socket 148. An example of a ferrule for affixing the tether 60 is found below in the discussion attendant to FIGS. 18 and 19.

The tether 60 is flexible and may be made of an absorbent material, taking on the form of woven fabric tubing, woven and non-woven mesh, or braided or woven structures. Growth factors or cells can be incorporated into the tether to promote bone growth along the tether 60. Growth factors can be transforming growth factor β1, insulin-like growth factor 1, platelet-derived growth factor, fibroblast growth factor, bone morphogenetic protein (BMP), LIM mineralization protein (LMP) and combinations thereof.

In FIGS. 16 through 20, a barbed anchor 61b is depicted according to an embodiment of the disclosure. The barbed anchor 61b includes many of the same components and attributes as the conical anchor 61a, which are indicated by same-numbered reference characters. The barbed anchor 61b is characterized by at least one barb 182 that projects radially. In some embodiments, the barb(s) 182 is tangentially continuous about the body axis 144 and includes an undercut 184. Both the conical anchor 61a and the barbed anchor 61b are examples of anchors 61 having body axes 144 that are linear and outer surfaces 138 that are axisymmetric about the body axis 144.

In some embodiments, the barbed anchor 61b defines an internal socket 202 that accepts a ferrule 204 in a press fit. The internal socket 202 may be defined distal to the mounting recess 156. For example, the internal socket 202 may define a socket opening 206 having a maximum radius R3 that is accessible from the distal surface 167 that bounds the frustoconical void 164. The internal socket 202 may be, but need not be, concentric about the mounting axis 158. In some embodiments, the internal socket 202 is frustoconical, defining a tapered surface 208 that defines an angle φ1 that slopes parallel to or away from the mounting axis 158 in the proximal direction 170, and defines a maximum radius R4 at a distal end of the tapered surface 208, with radius R4 being less than radius R3. In some embodiments, the angle φ1 is within a range that is from zero degree inclusive to less than four degrees. In some embodiments, the angle φ1 is within a range that is from zero degree inclusive to less than three degrees. In some embodiments, the angle φ1 is within a range that is from one degree inclusive to less than three degrees. Herein, a range having a limit that is said to be "inclusive" includes the inclusive endpoint value(s) of the range.

In some embodiments, the ferrule 204 includes a body 220 having a central axis 222 and including a proximal face 224 having a maximum radius r3, a distal face 226 having a maximum radius r4, and an outer surface 228 that extends from the proximal face 224 to the distal face 226. The ferrule 204 may also define an open slot 232 that extends through the proximal face 224 and the distal face 226, the open slot 232 also passing through the outer surface 228 on one side. In some embodiments, the open slot 232 extends into the body 220 far enough to pass through the central axis 222 and defines a gap 234 having a tangential dimension 236.

The ferrule 204 may define a tether socket 238 accessible from the distal face 226, the tether socket 238 having a radial dimension 242 that is greater than the tangential dimension 236 of the gap 234. The tether socket 234 extends axially into the body 220 of the ferrule 204 to define a shoulder 244 at the transition between the tether socket 238 and the gap 234. In some embodiments, the outer surface 228 is tapered to define an angle ϕ2 relative to the central axis 222. For the ferrule 204, the angle ϕ2 slopes away from the central axis 222 from the distal face 226 to the proximal face 224. In some embodiments, the angle ϕ2 is within a range of zero degree inclusive to four degrees inclusive. In some embodiments, the angle ϕ2 is within a range of zero degree inclusive to three degrees inclusive. In some embodiments, the angle ϕ2 is within a range of greater than one degree to two degrees inclusive. An angle ϕ2 that is zero corresponds to the outer surface 228 extending parallel to the central axis 222.

In some embodiments, the angle ϕ2 is greater than the angle ϕ1 of the tapered surface 208 of the internal socket 202 of the barbed anchor 61b, with the maximum radius r3 at the proximal face 224 of the ferrule 204 being greater than the maximum radius R3 at the socket opening 206 of the internal socket 202, whereas the maximum radius r4 of the distal face 226 of the ferrule 204 is less than the maximum radius R3 at the socket opening 206 of the internal socket 202.

In assembly, a knot 252 may be formed proximate an end of the tether 60 and disposed in the tether socket 234, the knot 252 being of greater radial dimension than the tangential dimension 236 of the gap 234. A portion 254 of the tether 60 (e.g., a portion adjacent the knot 252) is slipped into the open slot 232 so that the tether 60 extends proximally from the ferrule 204. The distal face 226 of the ferrule 204 is inserted through the socket opening 206 and the ferrule 204 pressed into the internal socket 202.

Functionally, the barb(s) 182 enhance the coupling between the anchor 61b and the bone of the endplate 92, 94. The arrangement of the ferrule 204 and internal socket 202 enables the tether 60 to be affixed to the barbed anchor 61b with the outer surface 138 of the anchor remaining continuous from the pointed distal extremity 134 to the proximal base surface 136. Because the knot 252 is of greater radial dimension than the tangential dimension 236 of the gap 234, the tether 60 will not slip through the gap 234, so that the knot 252 is captured within the tether socket 234 between the shoulder 244 of the ferrule 204 and the internal socket 202.

In some embodiments, the angle ϕ1 facilitates the press fit of the ferrule 204, and is dimensioned so as not to be self-releasing with the angle ϕ2 of the outer surface 228 of the ferrule 204. For embodiments where the maximum radius r3 at the proximal face 224 of the ferrule 204 is greater than the maximum radius R3 at the socket opening 206 of the internal socket 202 and the maximum radius r4 of the distal face 226 of the ferrule 204 is less than an the maximum radius R3 at the socket opening 206 of the internal socket 202, the distal face 226 of the ferrule 204 can be freely inserted into the socket opening 206 for guiding and alignment within the internal socket 202, while providing an interference fit with the internal socket 202 as the maximum radius r4 of the proximal face 224 of the ferrule 204 is driven into the smaller maximum radius R4 of the socket opening 206. The open slot 232 facilitates compression of the ferrule 204 within the internal socket 204, enabling the ferrule 204 to contract tangentially. The resilience of the ferrule 204 within the internal socket 202 provides friction between the ferrule 204 and the internal socket 202 that secures the ferrule 204 and tether 60 to the barbed anchor 61b.

The tangential contraction of the ferrule 204 reduces the tangential dimension 236 of the gap 234 which, in some embodiments, acts to cinch the ferrule 204 onto the tether 60. Accordingly, in some embodiments, the tether 60 is secured to the ferrule 204 by merely holding an end of the tether 60 within the open slot 232 as the ferrule 204 is driven into the internal socket 204 (i.e., without need for forming the knot 252).

The ferrule 204 and anchor 61 may be fabricated from a biocompatible metal such as titanium, tantalum, or NITI-NOL. Based on the disclosure provided, the person of ordinary skill in the art will recognize the arrangement of the ferrule 204 within the internal socket 202 of the barbed anchor 61b can be implemented with the conical anchor 61a. Likewise, based on the disclosure provided, the external tether receptacle 146 of the conical anchor 61a can be implemented for the barbed anchor 61b.

The distal end portion 64 of the plunger arm 42 is formed to accommodate the shape of the mounting recess 156 of the anchor 61 while enabling a ready release between the anchor 61 and the distal end portion 64. For anchors 61 having the frustoconical void 164, such as the conical anchor 61a and the barbed anchor 61b, the distal end portion 64 may be formed generally in the shape of a frustum 270 (FIG. 20), the frustum 270 being centered about an actuation axis 272 and having a tapered surface 274 with the same shape (e.g., same angle ϕ as the frustoconical void 164) as the tapered surface 166 that bounds the frustoconical void 164. The frustum 270 may be undersized relative to the frustoconical void 164. The distal end portion 64 may define an open slot 276 that extends axially therethrough and is recessed from said tapered surface 272, the slot 276 thereby being accessible through the tapered surface 272 of the distal end portion 64.

Functionally, undersizing the frustum 270 relative to the frustoconical void 164 facilitates easy release of the anchor 61 from the plunger arm 42. The open slot 274 accommodates passage of the tether 60 that depends from the barbed anchor 61b. The angle β is sized to be self-releasing. In some embodiments, the self-releasing angle β is within a range of 5 degrees inclusive to 45 degrees inclusive. In some embodiments, the self-releasing angle β is within a range of 5 degrees inclusive to 15 degrees inclusive. In some embodiments, the self-releasing angle β is within a range of 6 degrees inclusive to 10 degrees inclusive. In some embodiments, the self-releasing angle β is within a range of 7 degrees inclusive to 9 degrees inclusive. In some embodiments, the self-releasing angle β is nominally 8 degrees.

Figure 21:
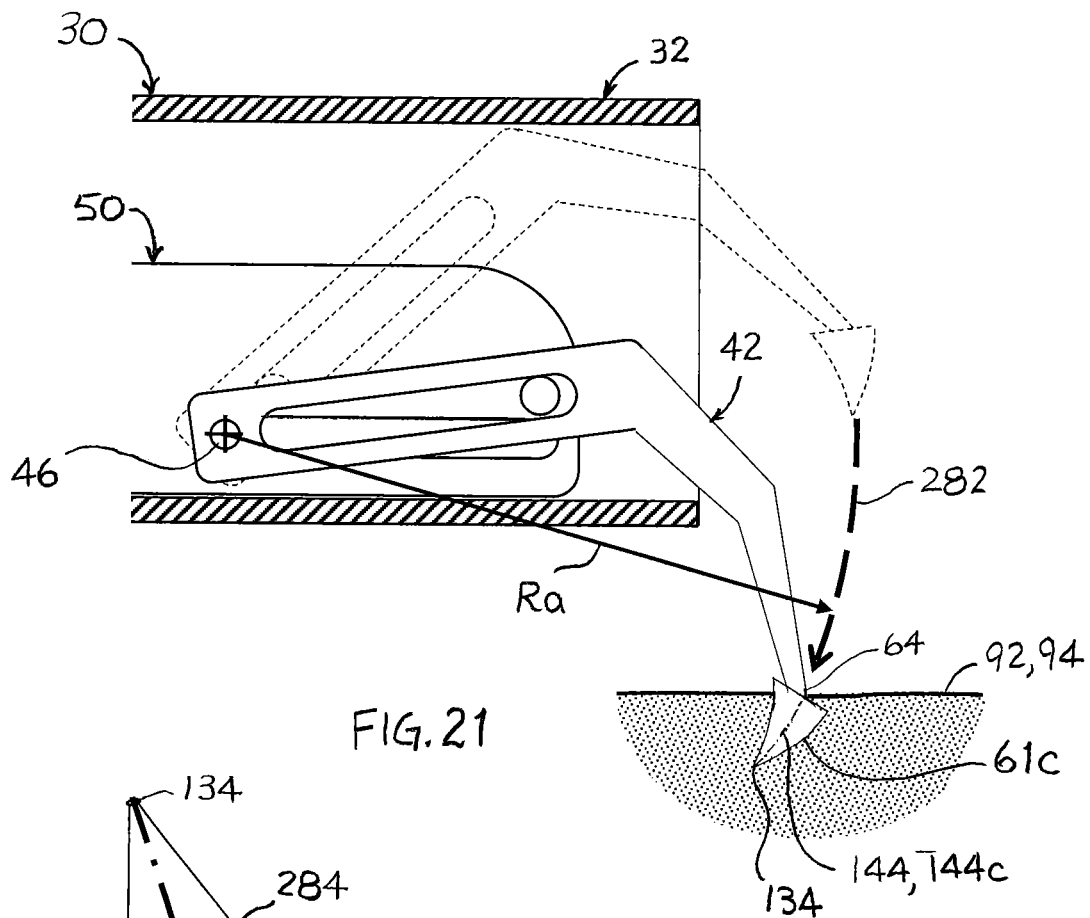
FIG. 21 is a partial sectional, side elevational view of the cannulated plunger assembly with an arcuate anchor being implanted into a vertebral end plate according to an embodiment of the disclosure.
Figure 22:
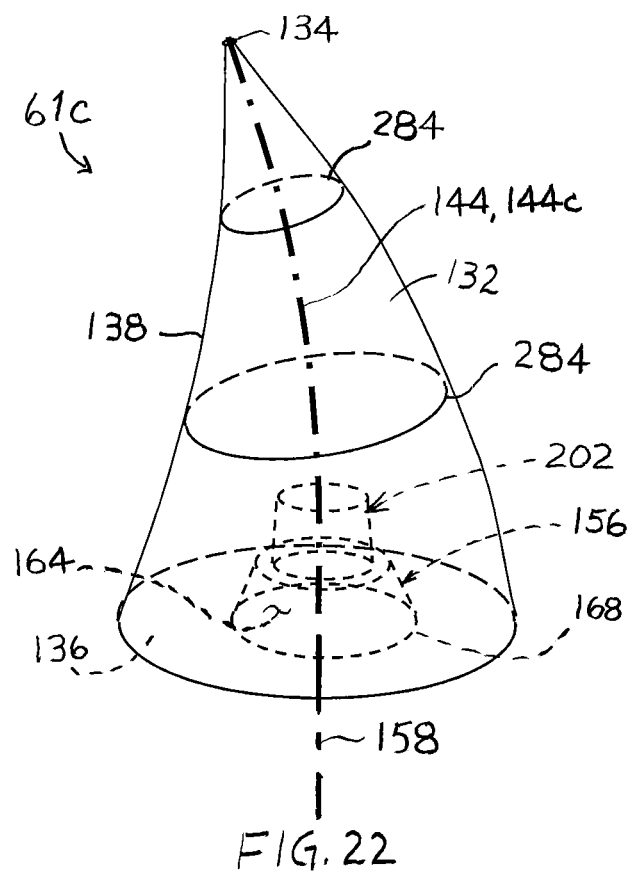
FIG. 22 is an enlarged, upper perspective view of the arcuate anchor of FIG. 21 according to an embodiment of the disclosure.

In FIGS. 21 and 22, an arcuate anchor 61c is depicted according to an embodiment of the disclosure. The arcuate anchor 61c includes many of the same components and attributes as the conical anchor 61a, which are indicated by same-numbered reference characters. The arcuate anchor 61c is characterized by an arcuate body axis 144c. In some embodiments, the distal end portion 64 of the plunger arm 42 is configured to cant the anchors 61 with respect to the plunger arm 42 so that the body axes 144 of the anchors 61 are generally aligned with an arc 282 through which the anchor 61 travels during deployment. In some embodiments, the arc 282 is defined by a radius Ra that extends from a center of the pin 46 of the plunger arm 42 to the pointed distal extremity 134 of the arcuate anchor 61c. Accordingly, the arcuate body axis 144c is defined along the same radius Ra so that arcuate body axis 144c is coincident with the arc 282 through which the arcuate anchor 61c passes.

The arcuate anchor 61c is characterized as having cross-sections 284 that are normal to the arcuate body axis 144c, leading to the arcuate shape. In effect, the arcuate anchor 61c is akin to the conical anchor 61*a* that is "bent" to conform to the arc 282. The arcuate anchor 61*c* may take other forms, such as the barbed anchor 61*b*.

Functionally, having the body axis 144 generally aligned with the arc 282 enables the pointed distal extremity 134 to penetrate the vertebral endplate 92, 94 in a substantially axial translation relative to the anchor 61, with limited or no lateral movement as the anchor 61 penetrates the vertebral endplate 92, 94. The substantially axial translation enables the anchor 61 to be driven efficiently into the vertebral endplate 92, 94 and provides a tighter and more effective grip between the anchor 61 and the bone of the vertebral endplate 92, 94.

In FIGS. 23 and 24, an arcuate anchor 61*d* with corresponding distal end portion 64 of the plunger arm 42 is depicted according to an embodiment of the disclosure. The arcuate anchor 61*d* includes many of the same components and attributes as the arcuate anchor 61*c*, which are indicated by same-numbered reference characters. The arcuate anchor 61*d* is characterized by a keyed recess 292. In the depicted embodiment, the keyed recess 292 includes a keyway 294. The distal end portion 64 of the plunger arm 42 may include an appendage 296 that conforms to and is received by the keyway 294. Other shapes may be utilized to provide a keyed recess, such as an oblong or polygonal shape.

Functionally, the keyed recess 292 and correspondingly shaped distal end portion 64 enable the arcuate anchor 61*d* to be mounted in a fixed rotational orientation relative to the mounting axis 158. This aspect has utility for asymmetric anchors such as the arcuate anchor 61*c*, 61*d* for alignment of the arcuate body axis 144*c* with the arc 282.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A plunger assembly for setting a tether with anchors affixed thereto for extending between adjacent vertebrae, the plunger assembly comprising:
   a tubular housing defining a central axis and having an open distal end;
   a pair of plunger arms disposed at least partially within said tubular housing, each of said plunger arms being mounted to a respective pivot pin, said pivot pins being mounted to and extending laterally through said tubular housing; and
   a drive assembly disposed in said tubular housing, said drive assembly configured to translate parallel to said central axis and toward said open distal end to rotate said pair of plunger arms from a retracted configuration to a deployed configuration,
   wherein:
     in said retracted configuration, said pair of plunger arms is surrounded by said tubular housing; and
     in said deployed configuration, said pair of plunger arms extends through said open distal end and beyond an outer radius of said tubular housing,
   wherein said drive assembly is coupled to said pair of plunger arms in a camming arrangement, and
   wherein said camming arrangement includes:
     a pair of cam slots, each defined in a corresponding one of said pair of plunger arms; and
     a pair of cam pins, each extending from said drive assembly and being disposed in a corresponding one of said pair of cam slots.

2. The plunger assembly of claim 1, wherein said camming arrangement includes:
   a pair of arcuate reliefs formed at a distal end of said drive assembly, each contacting a corresponding one of said pair of plunger arms to drive said plunger arms from said retracted configuration into said deployed configuration.

3. The plunger assembly of claim 1, comprising an actuation handle affixed to a proximal end of said tubular housing, said actuation handle being coupled to said drive assembly for translation of said drive assembly along said central axis.

4. The plunger assembly of claim 3, wherein said actuation handle is a KERRISON handle.

5. The plunger assembly of claim 1, wherein each of said pair of plunger arms includes a distal end portion configured to accept a respective anchor.

6. The plunger assembly of claim 5, wherein said distal end portion is configured to cant said respective anchor with respect to the plunger arm to generally align said anchor with an arc through which said anchor travels during deployment.

7. The plunger assembly of claim 6, wherein said distal end portion includes a tapered surface for release of said anchor.

8. The plunger assembly of claim 7, wherein said distal end portion is shaped as a frustum.

9. The plunger assembly of claim 8, wherein said frustum defines an open slot that is recessed from said tapered surface.

10. The plunger assembly of claim 7, wherein said tapered surface defines an angle relative to an actuation axis of said distal end portion, said angle being within a range of 5 degrees inclusive to 45 degrees inclusive.

11. The plunger assembly of claim 10, wherein said angle is within a range of 5 degrees inclusive to 15 degrees inclusive.

12. The plunger assembly of claim 10, wherein said angle is within a range of 6 degrees inclusive to 10 degrees inclusive.

13. The plunger assembly of claim 10, wherein said angle is within a range of 7 degrees inclusive to 9 degrees inclusive.

14. The plunger assembly of claim 10, wherein said angle is nominally 8 degrees.

\* \* \* \* \*